United States Patent

Bruckner et al.

Patent Number: 6,068,591
Date of Patent: May 30, 2000

[54] PUBO-URETHRAL SUPPORT HARNESS APPARATUS FOR PERCUTANEOUS TREATMENT OF FEMALE STRESS URINARY INCONTINENCE

[76] Inventors: Norman I. Bruckner, 3432 Brookshire Dr., Plano, Tex. 75075; Guillermo H. Davila, 8544 E. Oregon Pl., Denver, Colo. 80231

[21] Appl. No.: 09/024,701

[22] Filed: Feb. 17, 1998

[51] Int. Cl.[7] .................................................. A61F 2/04
[52] U.S. Cl. ............................................ 600/30; 606/151
[58] Field of Search ................ 600/29–30; 128/DIG. 25, 128/884, 885, 830; 606/139, 141, 151, 216

[56] References Cited

U.S. PATENT DOCUMENTS

| | | | |
|---|---|---|---|
| 5,013,292 | 5/1991 | Lemay | 600/30 |
| 5,112,344 | 5/1992 | Petros | 600/30 |
| 5,256,133 | 10/1993 | Spitz | 600/30 |
| 5,647,836 | 7/1997 | Bake, III et al. | 600/30 |

*Primary Examiner*—John P. Lacyk

[57] ABSTRACT

An apparatus for treatment of female stress urinary incontinence (SUI) with a support harness adapted to fit over the superior edge of the pubic bone of a patient, left or right of the pubis symphysis, a stay adapted to rest against the anterior vaginal wall at the level of the urethrovesical junction, and vaginal shaft connecting the stay to the support harness and adapted to elevate the stay causing elevation of the anterior vaginal wall.

18 Claims, 7 Drawing Sheets

PUBO-URETHRAL SUPPORT HARNESS APPARATUS FOR PERCUTANEOUS TREATMENT OF FEMALE STRESS URINARY INCONTINENCE

BACKGROUND OF THE INVENTION

This invention relates to medical devices as alternatives for surgical correction of anatomic female stress urinary incontinence and more particularly to a Pubo-Urethral Support Harness Apparatus (referred to as a "PUSH apparatus") for Percutaneous Treatment of Female Stress Urinary Incontinence.

The present invention relates to female stress urinary incontinence (SUI) and provides an apparatus and method for treatment. More specifically, this invention relates to an apparatus and method of elevating and supporting the urethrovesical junction without use of sutures, staples or bone anchors to correct female stress urinary incontinence.

Anatomic SUI is a condition that is accompanied by the involuntary loss of urine during coughing, laughing, sneezing or other exertional physical activities. SUI is most often caused by weakening of the supporting endopelvic fascia and muscles resulting in the abnormal descent of the urethra and bladder neck with increased intra-abdominal pressure. Continence is re-established by bladder neck elevation and stabilization in its physiologic position.

SUI interferes with a woman's ability to lead a normal life. SUI impacts a woman's self-esteem, often leads to embarrassment and limits her capacity to fulfill her social and family roles. Women address this condition by: managing the problem with absorbent products; undergoing non-surgical treatments such as behavior training, drugs, and using vaginal anatomical support devices; or undergoing surgical intervention. Disadvantages associated with managing the symptoms of SUI include odor and alteration of dress to conceal the presence of a pad or brief. Among the disadvantages associated with non-surgical therapies are poor response to treatment, inconvenience, the need for the patient to be highly motivated, and vaginal discomfort caused by the presence of a support device.

Many surgical procedures involving urethrovesical elevation have been devised over the years to cure SUI. Robertson, U.S. Pat. No. 5,019,032 describes a method of treatment involving the installation of sutures between the rectus fascia and the vagina using a needle inserted through the abdomen. A urethropexy procedure is disclosed in U.S. Pat. No. 5,013,292 to Lemay and describes burying a pair of implants, one on each side of the pubis symphysis, and threading suture from the vagina through the implants to support the bladder neck. Alternatively, the ends of the sutures can be tied to a saddle member to support the bladder neck. Richardson, U.S. Pat. No. 5,149,329 described elevation of the urethrovesical junction by bringing the paravaginal fascia into juxtaposition with Cooper's ligament through suture placement using a suturing needle assembly. Petros, U.S. Pat. No. 5,112,344 describes looping a filamentary element between the vaginal wall and the rectus abdominis in the anterior wall of the abdomen to provide urethrovesical elevation. Several common needle suspension procedures for treating SUI have been disclosed over the years including: Pereyra (e.g., West J. Surg. Obst. & Gynec., ppg. 223–226, 1959) in which suture interconnects subcutaneous tissue above the rectus fascia to tissue on both sides of the urethra; Raz (e.g. Urol., Vol. 17 ppg., 82–85, 1981) in which suture interconnects subcutaneous tissue above the rectus fascia to the vaginal wall on both sides of the urethra; and Stamey (e.g., Surg. Gyn. & Obst., Vol. 136, ppg. 547–554, April 1973) in which Dacron sleeves, located in tissue on both sides of the urethra are attached to subcutaneous tissue above the rectus fascia. Problems associated with many of these procedures result in suture pull through from the abdominal wall rectus fascia causing reoccurrence of incontinence. In addition, these procedures generally require general anesthesia, lengthy hospitalization and restricted activities for 8 to 12 weeks.

An apparatus for treating SUI by applying an anchoring device to body tissue and adjusting the suture length between anchors using a cinching member is described in U.S. Pat. No. 5,562,689 to Green et al. Blake, U.S. Pat. No. 5,647,836 discloses the use of anchor pairs, each pair interconnected by suture to treat SUI. Endopelvic fascia attached to each side of the urethra is elevated and held in place by a pair of anchors comprised of upper and lower stays, whereby the upper stay is positioned above the rectus fascia. Benderev, U.S. Pat. No. 5,611,515 describes a bladder neck suspension procedure using anchor fixation of the suspending sutures to the pubic bone, and the tools required to perform the procedure. The concerns with this technique include development of osteomyelitis (bone infection) and vaginal wall pull through leading to surgical failure.

Although surgery provides the highest success rates among all treatments for SUI, it is not without its problems. Reported drawbacks to surgical therapy include: expenses due to the associated medical and hospitalization costs; possible medical complications such as bleeding and alteration of normal voiding; impact on short-tern normal life style activities; and in some instances, require women to modify their life style permanently to retain their continence. Surgery may also require repeat surgery in order to maintain continence.

SUMMARY OF THE INVENTION

The primary object of the invention is to provide effective, long-lasting, therapy for SUI that has minimal impact on life style activities.

Another object of the invention is to provide a treatment for SUI that is not prone to medical complications.

Another object of the invention is to provide a treatment for SUI that does not require bone anchors, sutures, staples, or peri-urethral injections for restoration of bladder neck anatomic support.

Yet another object of the invention is to provide a treatment for SUI that is simple, easily-learned, minimally invasive and can be performed as an outpatient procedure under local or mild general anesthesia with no post-treatment catheterization.

A further object of the invention is to provide a treatment for SUI that is, if necessary, amenable to adjustment without repeat major surgery.

Another object of the invention is to provide a treatment for SUI that can be performed on women with previous unsuccessful anti-incontinence surgery.

Still yet another object of the invention is to provide a treatment for SUI that can be performed along with other pelvic reconstructive procedures.

Other objects and advantages of the present invention will become apparent from the following descriptions, taken in connection with the accompanying drawings, wherein, by way of illustration and example, an embodiment of the present invention is disclosed.

The present invention comprises an apparatus and a minimally invasive method for treating SUI by elevating the anterior vaginal wall on each side of the urethra, thereby supporting the urethrovesical junction. The treatment can be performed in an office or as an outpatient procedure with local or mild general anesthesia without use of sutures, staples, bone anchors or peri-urethral injectable bulking agents. The apparatus described in this invention possess fixably adjustable design features that compensate for anatomic changes that could occur post-operatively and cause incontinence to reoccur.

In accordance with an embodiment of the present invention, an apparatus for treatment of SUI comprises: a support harness adapted to fit over the superior edge of the pubic bone of a patient, to the left of the pubis symphysis, a stay adapted to rest against the anterior vaginal wail of a patient or positioned submucosally at the level of the urethrovesical junction, and a shaft connecting the stay to the support harness and adapted to elevate the stay causing elevation of the anterior vaginal wall. In other embodiments, the support harness and shaft may be of a unitary piece design, the shaft and stay may be of a unitary piece design, or the support harness, shaft and stay may be of a unitary piece design. A second apparatus comprising of similar components is positioned to the right of the pubis symphysis. The harness component of the apparatus may be constructed of a material that is shapeable and possesses features for fitting securely over and against the pubic bone. The shaft component may be constructed of shapeable material including wire or metal thread.

In accordance with another embodiment of the invention, a kit for the treatment of SUI comprises two multi-component apparatus for bladder neck elevation, at least one delivery system adapted for the placement of the support harness component of the apparatus, at least one delivery system adapted for the placement of the shaft component of the apparatus, and at least one apparatus assembly tool adapted for uniting apparatus components. In alternate embodiments, the multi component apparatus may be a single component type that may require a single delivery system.

In accordance with another embodiment of the invention, a method for the treatment of SUI comprises the steps of: (a) Placing patient in the lithotomy position, (b) Assembling a stay and vaginal shaft and loading the assembled apparatus into a cannula delivery unit, (c) Penetrating the anterior vaginal wall with the sharp closed leading end of the loaded cannula delivery unit at a location approximately 2 cm lateral to the urethrovesical junction, (d) Directing the cannula delivery unit in a cephalad direction with the leading end adjacent to the posterior aspect of the pubic bone, (e) Making a small suprapubic incision lateral to the midline on the same side as the placement of the cannula delivery unit, (f) Delivering the cannula delivery unit through the incision, (g) Removing the cannula delivery unit suprapubically, confirming that the stay is correctly and firmly positioned against the anterior vaginal wall, (h) Raising the stay-vaginal shaft through the suprapubic incision to an appropriate tension, (i) Attaching the stay-vaginal shaft to the support harness unit at the suprapubic incision site, (j) Placing the now formed PUSH apparatus over the superior edge of the pubic bone with the shaft and support harness fixably adjustable site on the superior aspect of the pubic bone and the inner serrated surface of the support harness on the anterior aspect of the pubic bone, (k) Adjusting the position of the vaginal shaft in the support harness to achieve the appropriate vaginal wall elevation; (l) Closing the suprapubic incision and, if required, trim excess shaft length before closing; and (m) Repeating steps b–l on the opposite side of the urethrovesical junction using the second PUSH apparatus.

In another embodiment, a method for the treatment of SUI comprises the steps of: (a) Placing patient in the lithotomy position, (b) Assembling a stay and support harness-vaginal shaft and loading the assembled apparatus into a cannula delivery unit, (c) Penetrating the anterior vaginal wall with the sharp closed leading end of the loaded cannula delivery unit at a location approximately 2 cm lateral to the urethrovesical junction, (d) Directing the cannula delivery unit in a cephalad direction with the leading end adjacent to the posterior aspect of the pubic bone, (e) Making a small suprapubic incision lateral to the midline on the same side as the placement of the cannula delivery unit, (f) Delivering the cannula delivery unit through the incision, (g) Removing the cannula delivery unit suprapubically, confirming that the stay is correctly and firmly positioned against the anterior vaginal wall, (h) Raising the support harness-vaginal shaft through the suprapubic incision to an appropriate tension, (i) Placing the now formed PUSH apparatus over the superior edge of the pubic bone with the vaginal shaft on the posterior aspect of the pubic bone and the inner serrated surface of the support harness on the anterior aspect of the pubic bone, (j) Adjusting the position of the stay on the vaginal shaft to achieve the appropriate vaginal wall elevation; (k) Trimming excess shaft length; (l) Closing the suprapubic incision; and (m) Repeating steps b–l on the opposite side of the urethrovesical junction using the second PUSH apparatus.

In another embodiment, a method for the treatment of SUI comprises the steps of: (a) Placing patient in the lithotomy position, (b) Forming a vaginal wall stay from the vaginal end portion of the PUSH apparatus; (c) Loading the single component PUSH apparatus into a cannula delivery unit, (d) Penetrating the anterior vaginal wall with the sharp closed leading end of the loaded cannula delivery unit at a location approximately 2 cm lateral to the urethrovesical junction, (e) Directing the cannula delivery unit in a cephalad direction with the leading end adjacent to the posterior aspect of the pubic bone, (f) Making a small suprapubic incision lateral to the midline on the same side as the placement of the cannula delivery unit, (g) Delivering the cannula delivery unit through the incision, (h) Removing the cannula delivery unit suprapubically, confirming that the stay is correctly and firmly positioned against the anterior vaginal wall, (i) Raising the PUSH apparatus through the suprapubic incision to an appropriate vaginal wall elevation, (j) Maintaining the appropriate vaginal wall elevation, advance the harness portion of the PUSH apparatus over the superior edge of the pubic bone and along the anterior aspect of the pubic bone so that the inner serrated surface of the support harness rests approximately halfway down the anterior aspect of the pubic bone; (k) Closing the suprapubic incision; and (m) Repeating steps b–k on the opposite side of the urethrovesical junction using the second PUSH apparatus.

In another embodiment, a method for the treatment of SUI comprises the steps of: (a) Placing patient in the lithotomy position, (b) Penetrating the anterior vaginal wall at a location approximately 2 cm lateral to the urethrovesical junction with the sharp leading end of a directional cannula delivery unit containing a support harness-vaginal shaft, (c) Directing the cannula delivery unit in a cephalad direction along the posterior aspect of the pubic bone over the superior edge of the pubic bone; (d) Advancing the harness end of the PUSH apparatus through the cannula delivery unit, down the anterior aspect of the pubic bone until the tip comes to rest at a position approximately halfway down the anterior aspect of the pubic bone, (e) Withdrawing the cannula delivery unit from the vagina exposing the tail of the vaginal shaft, (f) Coupling a stay on the vaginal shaft, (g) Adjusting the position of the stay against the anterior vaginal wall until the appropriate vaginal wall elevation is achieved, (h) Securing the position of the stay and trimming excess vaginal shaft from the PUSH apparatus, and (i) Repeat steps b–h on the opposite side of the urethrovesical junction using a second PUSH apparatus.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
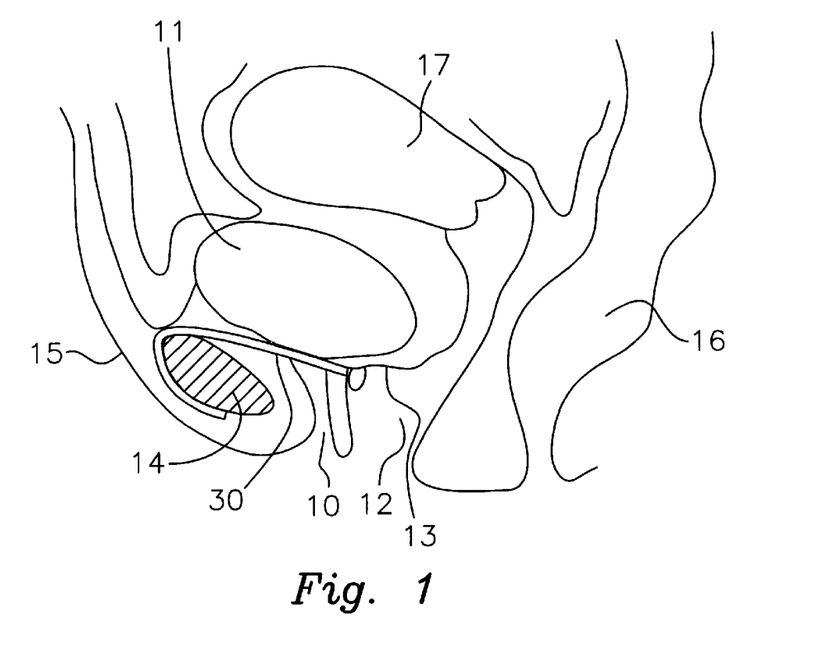
FIG. 1 is a lateral view of female pelvic anatomy with PUSH apparatus in accordance with the present invention in place.
Figure 2:
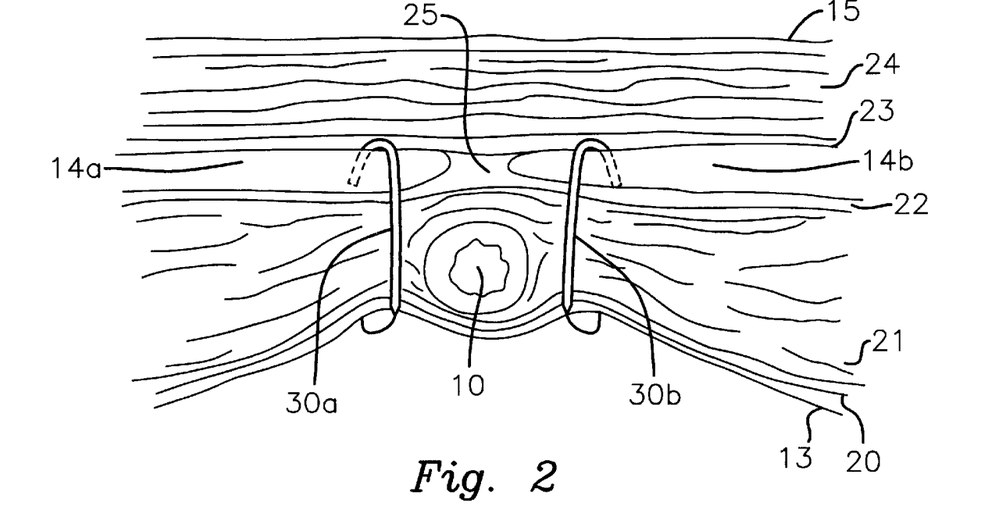
FIG. 2 is a cross-sectional view of urethra with two PUSH apparatus in accordance with the present invention in place.
Figure 3:
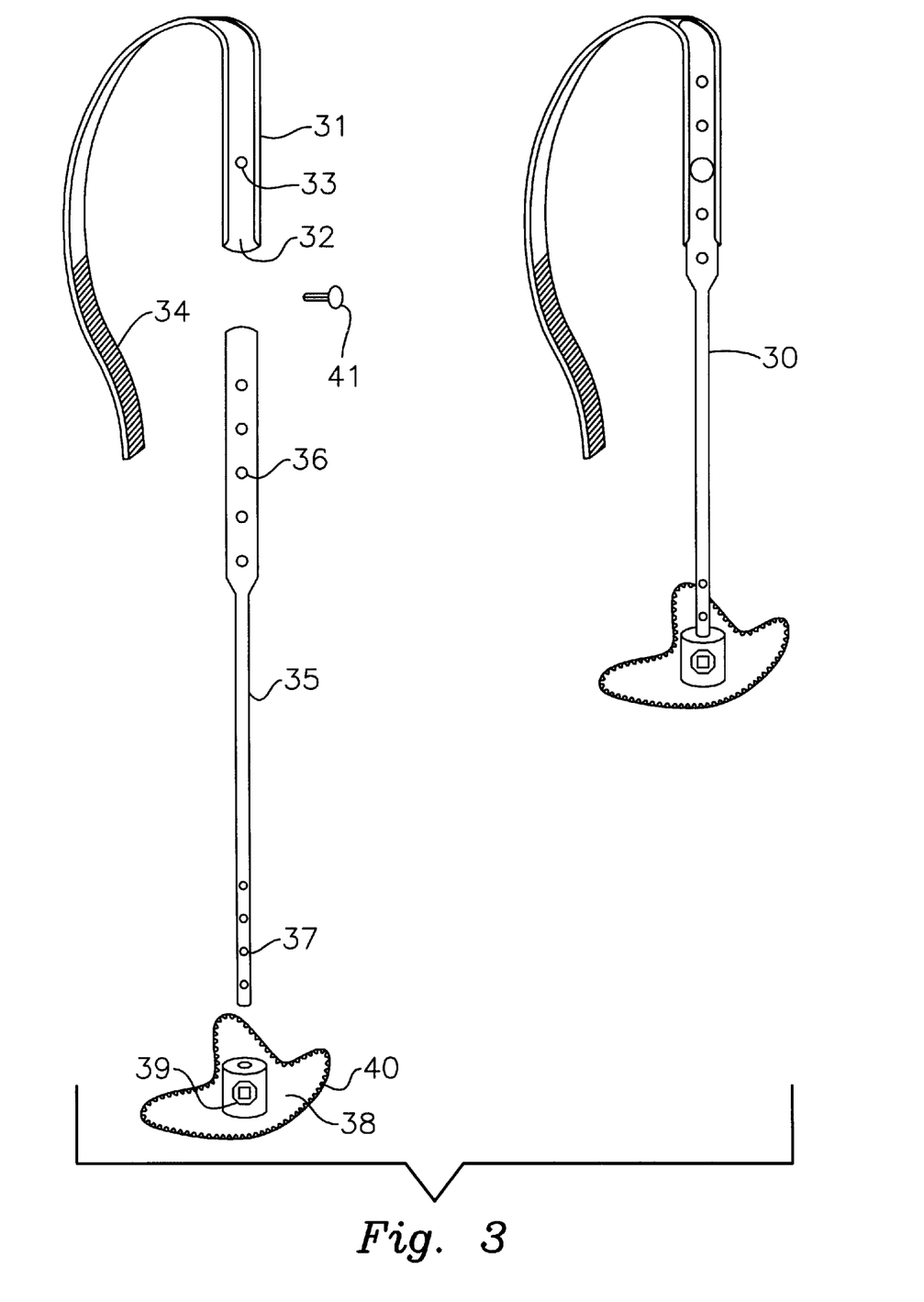
FIG. 3 is a perspective view of the support harness, vaginal shaft, and stay in a fixably adjustable relation according to an embodiment of the present invention.

Turning first to FIG. 1 there is shown a lateral view of the female pelvic anatomy identified by parts including urethra 10, bladder 11, vagina 12, vaginal wall 13, pubic bone 14, abdominal skin 15, rectum 16 and uterus 17, and the pubo-urethral support harness (referred to as a "PUSH apparatus") 30 positioned to elevate and support the urethrovesical junction. As shown in FIGS. 1 and 3, that portion of the PUSH apparatus 30 that fits over the pubic bone is referred to as the "support harness" 31; the part of the apparatus resting up against the anterior vaginal wall is referred to as the "stay" 38, and the segment of the PUSH apparatus connecting the support harness to the stay is referred to as the "vaginal shaft" 35. FIG. 2 shows a cross sectional view of the urethra 10 including surrounding vaginal mucosa 20, endopelvic fascia 21, rectus muscle 22, rectus fascia 23, subcutaneous tissue 24 and two PUSH apparatus 30a and 30b, each positioned over the pubic bone, left 14a and right 14b of the pubis symphysis 25, both functioning to elevate the anterior vaginal wall on their respective side of the urethra, thereby providing support to the urethra and bladder neck. The degree of vaginal wall elevation is dependent on the position of the stay relative to the pubic bone and is optimized by the fixably adjustable relation between PUSH apparatus components whereby the relative positioning may be adjustable but fixed once adjusted to the desired positional relationship and may be re-adjusted and fixed in the re-adjusted relation.

In accordance with the present invention, FIG. 3 shows a preferred embodiment of the invention. PUSH apparatus 30 is presented as three components: support harness 31; vaginal shaft 35; and stay 38. Vaginal shaft 35 and stay 38 are assembled by inserting the shaft 35 into the stay 38 and securing its position by engaging the stay locking nut 39, or other suitable mechanism such as a locking clip, into one of the stay fixably adjustable settings 37 on the shaft.

In operation and insertion, the assembled unit may be loaded into a cannula not shown but known to those in the art. The anterior vaginal wall located approximately 2 cm. lateral to the urethrovesical junction is penetrated with the sharp closed leading end of the loaded cannula. The cannula is directed in a cephalad direction with the leading end adjacent to the posterior aspect of the pubic bone 14 through a small suprapubic incision made lateral to the midline on the same side as the placement of the loaded cannula. The cannula is removed through the suprapubic incision and the position of the stay is confirmed such that the serrated surface 40 rest firmly against the anterior vaginal wall. Next, the stay-vaginal shaft unit is raised through the suprapubic incision until the appropriate vaginal wall 13 elevation is achieved. The support harness 31 is positioned above the pubic bone and the stay-vaginal shaft unit is inserted into the shaft receiver housing unit 32. Once the harness/shaft locking unit 33 and a vaginal shaft fixably adjustable setting 36 has been properly aligned, the two units are secured with Carter pin 41. Other suitable coupling devices include, but are not restricted to, alignment pins and screws. The support harness 31 of the assembled PUSH apparatus 30 is positioned over the superior edge of the pubic bone 14 with the vaginal shaft 35 on the posterior aspect of the pubic bone 14 and the harness serrated surface 34 resting against the anterior aspect of the pubic bone 14. Following the same procedure, a second PUSH apparatus is positioned on the opposite side of the urethra to produce the desired effect pictured in FIG. 2. Final adjustments are made to achieve the desired vaginal wall elevation using one or both fixably adjustable relation sites on each PUSH apparatus.

Figure 4:
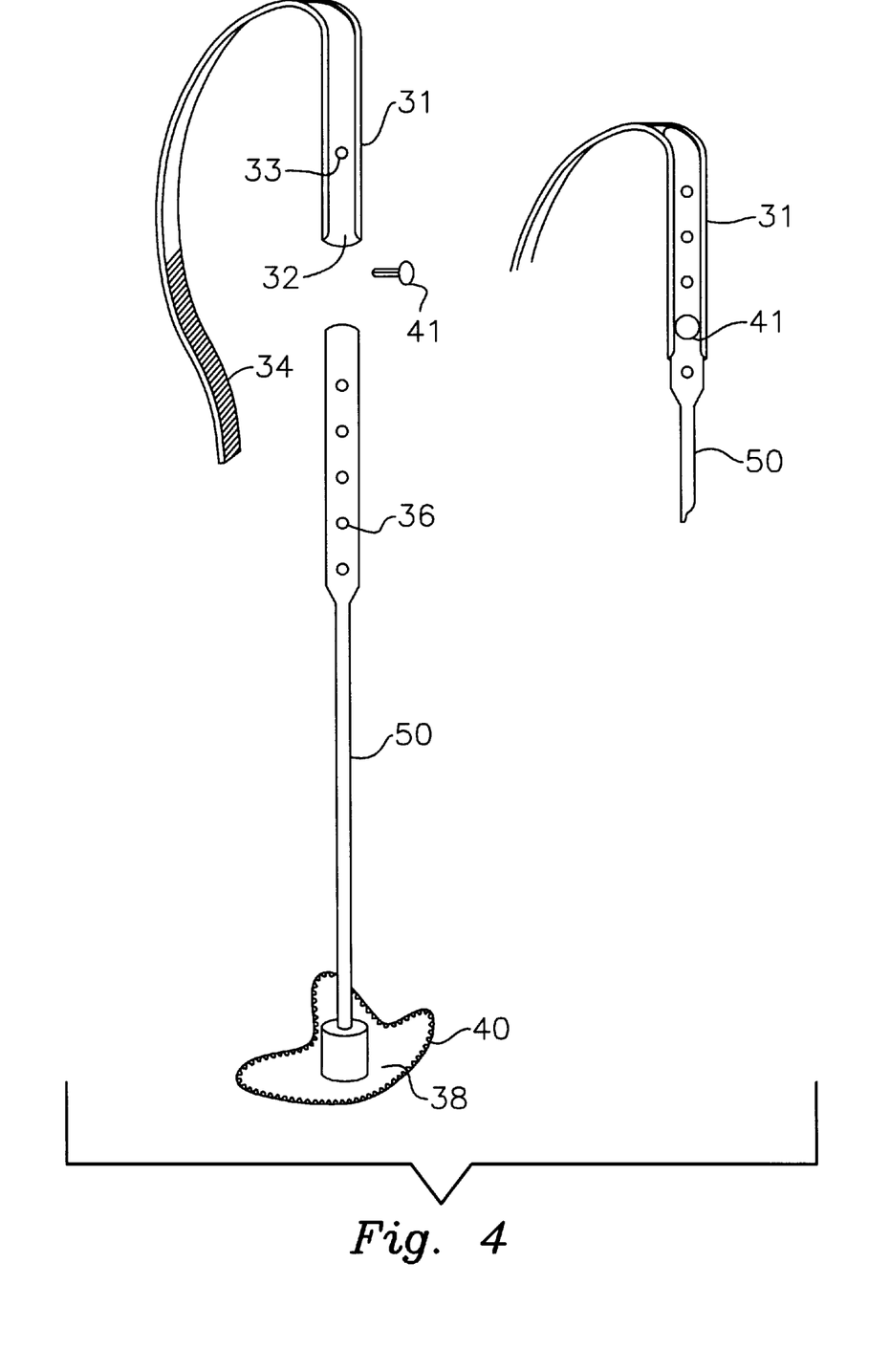
FIG. 4 is a perspective view of the support harness and vaginal shaft with stay in a fixably adjustable relation according to an embodiment of the present invention.

FIG. 4 illustrates a PUSH apparatus assembled from two components. In this presentation the PUSH apparatus is comprised of the support harness 31 and single component vaginal shaft-stay unit 50. Placement of this PUSH apparatus is achieved in the same manner as previously described in the preferred embodiment. Vaginal wall elevation adjustments are made using the fixably adjustable relation between the support harness and vaginal shaft-stay unit.

Figure 5:
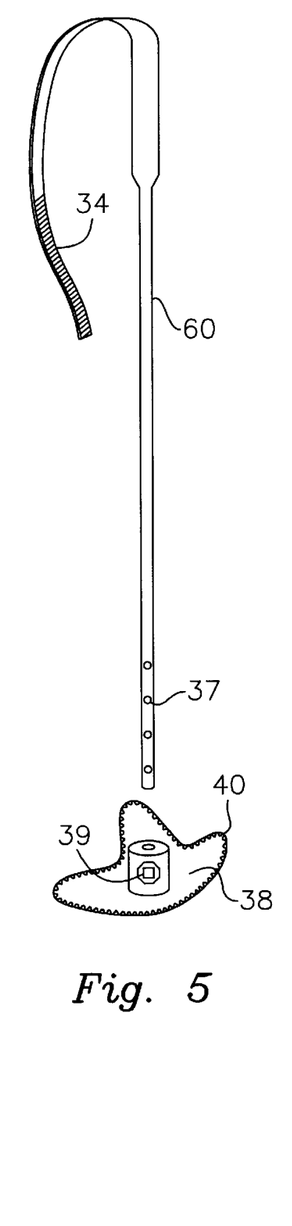
FIG. 5 is a perspective view of the support harness with vaginal shaft and stay in a fixably adjustable relation according to an embodiment of the present invention.

Illustrated in FIG. 5 is another embodiment of the invention comprising of a single unit support harness-vaginal shaft 60 and separate stay 38. The single unit support harness-vaginal shaft possesses a support harness serrated surface 34 and stay fixably adjustable settings 37. Placement of the PUSH apparatus is accomplished in the same manner as previously described. Once the cannula has been removed and the support harness-vaginal shaft has been raised through the suprapubic incision, the support harness portion of the support harness-vaginal shaft is directed to fit over the superior edge of the pubic bone 14. The stay is attached to the vaginal shaft portion of the support harness-vaginal shaft and elevated until the appropriate anterior vaginal wall elevation is achieved. Adjustment of the vaginal wall elevation is made using the fixably adjustable relation between the support harness-vaginal shaft component and the stay. In this embodiment of the invention, the support harness-vaginal shaft is envisioned as being constructed from a shapeable, superelastic or thermomemory material. Alternatively, placement of the support harness-vaginal shaft unit is accomplished using a directionally controlled cannula delivery unit. This procedure eliminates the need for a suprapubic incision to position the support harness.

Figure 6:
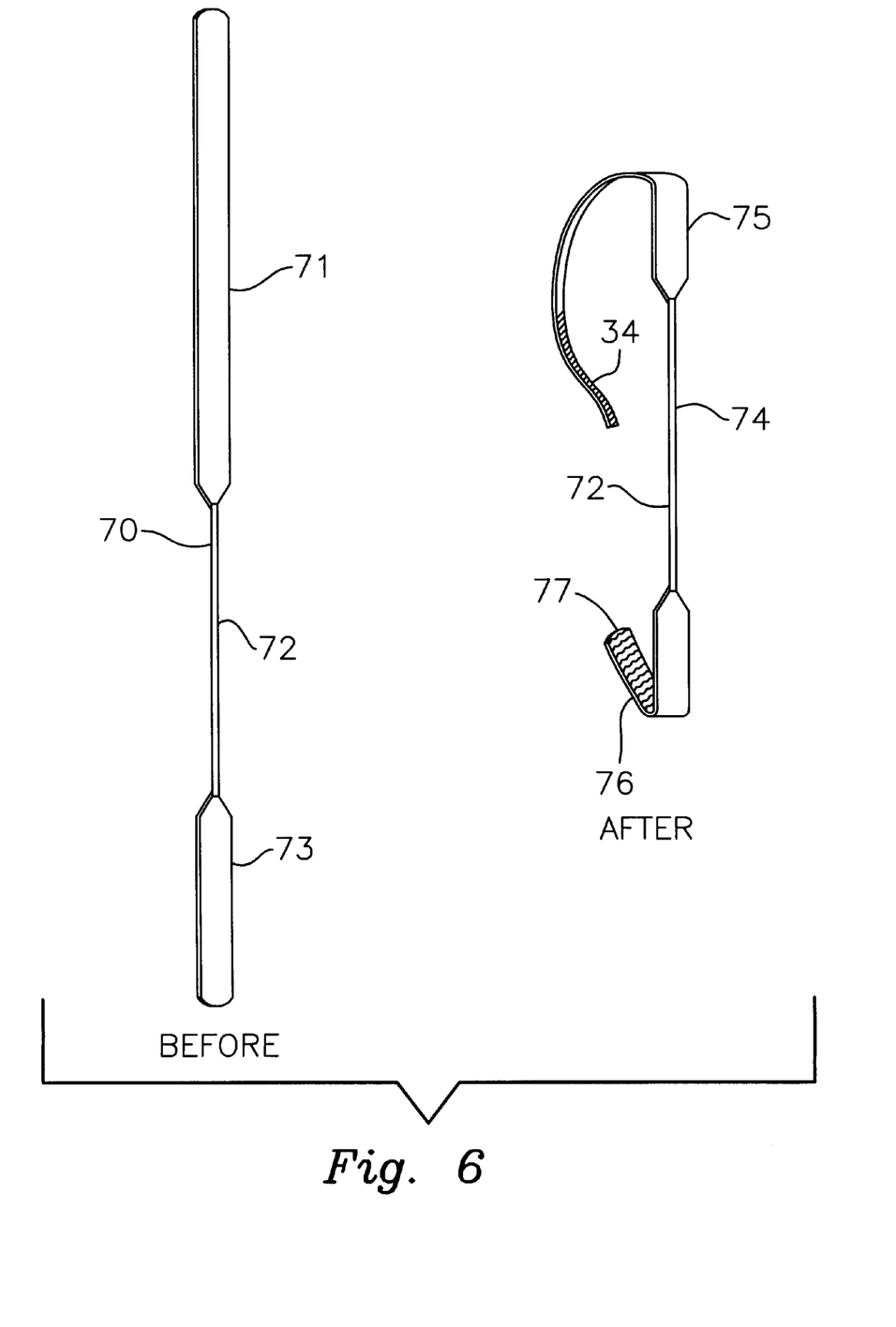
FIG. 6 is a perspective view of a single component PUSH apparatus before and after placement according to an embodiment of the present invention.

Turning to FIG. 6 there is shown a PUSH apparatus 74 produced from a single component unit 70 that contains within its structure a support harness segment 71, a vaginal shaft segment 72, and stay segment 73. Formation of this embodiment requires that one or more segments of the single component unit 70 be constructed from one or a combination of materials well known possessing shapeable, superelastic or thermomemory properties so that support harness 75 and stay 76 can be formed and/or manipulated to produce and maintain the desired vaginal wall elevation. Placement of the single component unit 70 is accomplished as previously described using a suprapubic incision to direct the support harness into position. However, prior to loading single component unit 70 into the cannula, stay 76 is formed. Once the cannula is removed and the stay is correctly and securely positioned with serrated surface 77 against the anterior vaginal wall, unit 70 is raised through the suprapubic incision until the appropriate elevation of the anterior vaginal wall is obtained. Maintaining the position of the vaginal wall 13, the leading end of unit 70 is allowed to conform to the shape of the pubic bone 14. The position of the newly formed support harness duplicates previous embodiments of the invention. Alternatively, stay 76 or another presentation, may be programmed into the single unit PUSH apparatus, thereby assuming its functional configuration once the cannula delivery unit is removed. Again, this PUSH apparatus negates the need for a suprapubic incision assuming use of a delivery unit with directional capabilities.

Figure 7:
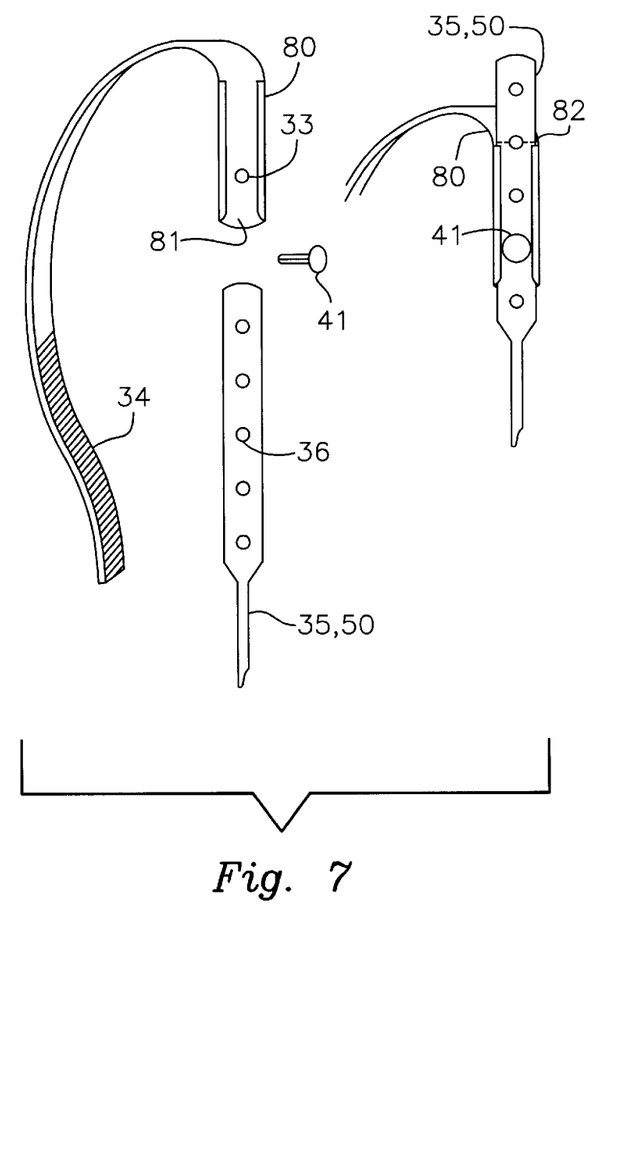
FIG. 7 is a perspective view of alternate fixably adjustable relation between support harness with open shaft receiver housing and vaginal shaft according to an embodiment of the present invention.

FIG. 7 represents another embodiment of the fixably adjustable relation between the vaginal shaft 35 and the support harness 31 presented in FIGS. 3 and 4. In these figures, support harness 31 has a closed shaft receiver housing 32, which requires the leading end of vaginal shafts 35 and 50 be shapeable for them to conform to the support harness 31. Support harness 80 illustrated in FIG. 7 has an open shaft receiver housing 81. In this presentation, once the appropriate vaginal wall elevation has been achieved and vaginal shaft 35 or 50 is secured in the shaft receiver housing, excess vaginal shaft is cut at position 82 just above and outside of the shaft receiver housing.

Figure 8:
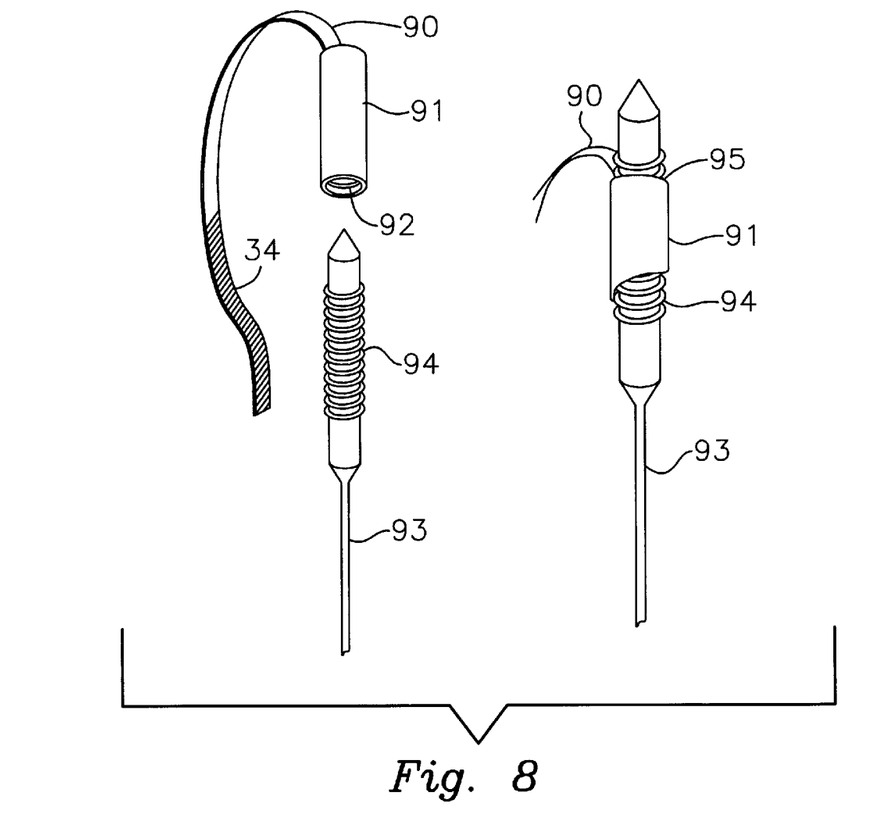
FIG. 8 is a perspective view of alternate fixably adjustable relation between support harness with cylindrical shaft receiver housing and vaginal shaft according to an embodiment of the present invention.

Illustrated in FIG. 8 is an other embodiment of the fixably adjustable relation between the vaginal shaft and the support harness presented in FIGS. 3 and 4. Support harness 90 is shown with threaded cylindrical shaft receiver housing 91. In this embodiment, elevation of the anterior vaginal wall is achieved by threading vaginal shaft 93 into housing 91. The complementary threads 92 and 94 secure shaft 93 in shaft receiver housing 91. Excess vaginal shaft is cut at position 95, located just above shaft receiver housing 91.

Figure 9:
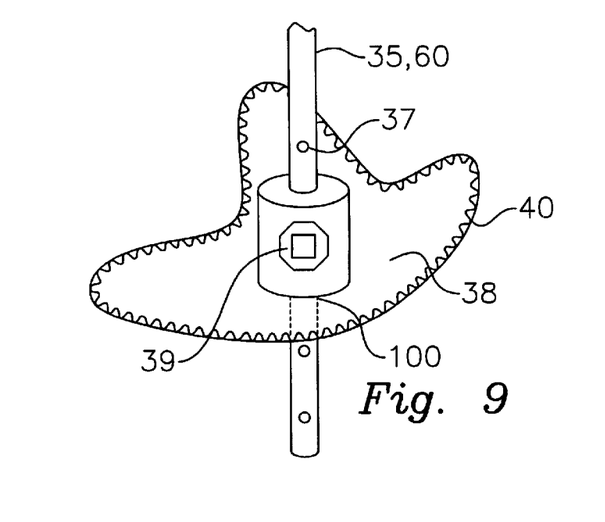
FIG. 9 is a perspective view of vaginal shaft and stay in fixably adjustable relation according to an embodiment of the present invention.

FIG. 9 shows an enlarged view of the fixably adjustable relation between stay 38 and vaginal shafts 35 and 60 presented in FIGS. 3 and 5, respectively. Excess vaginal shaft is removed at cut line 100. Alternatives to stay locking nut 39 include, but not restricted to, devices such as Carter pins, alignment pins or clips.

Figure 10:
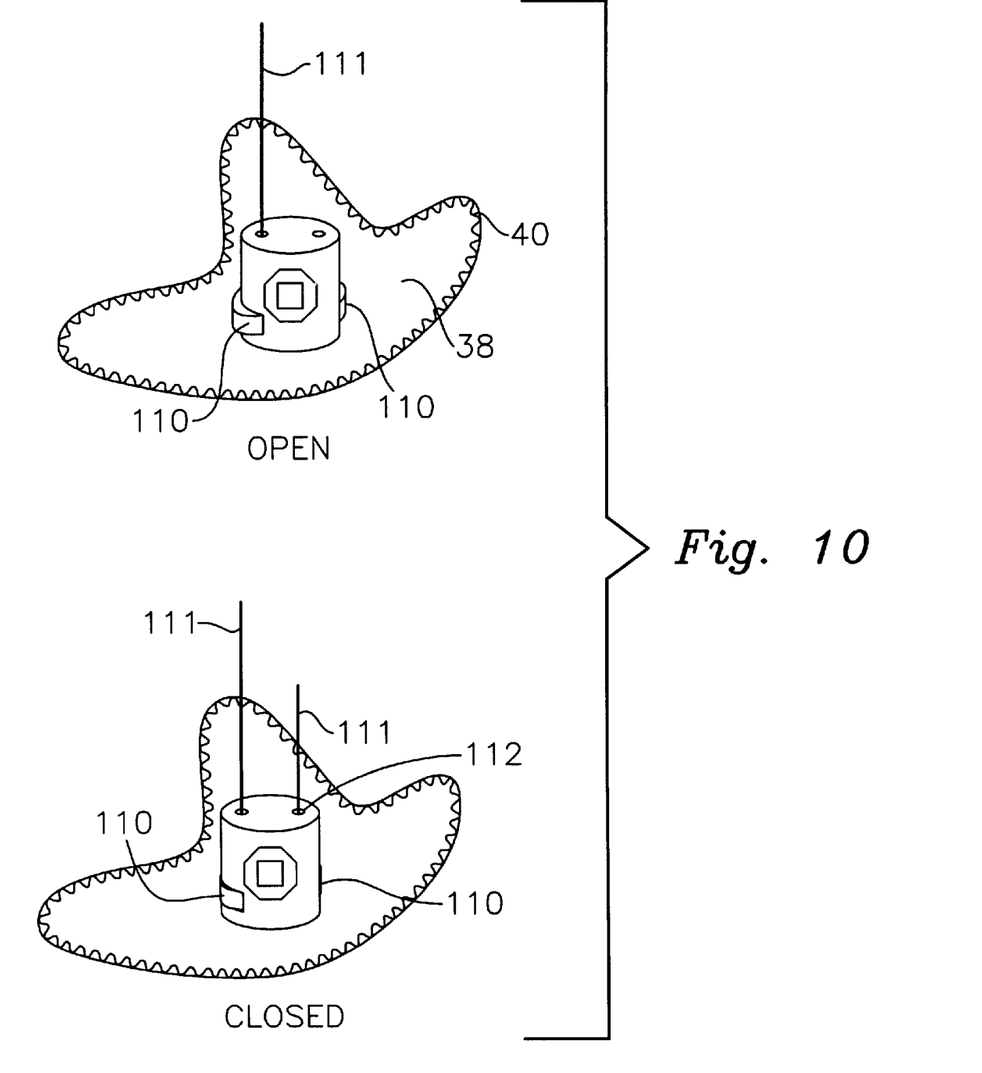
FIG. 10 is a perspective view of vaginal shaft constructed of wire or metal thread and stay in a fixably adjustable relation according to an embodiment of the present invention.

In those embodiments of the present invention where the vaginal shaft or vaginal shaft portion of the support harness is wire or metal thread, the fixably adjustable relation between stay 38 and vaginal shaft 111 is illustrated in FIG. 10. Again, once the appropriate elevation of the anterior vaginal wall has been achieved, the position of stay 38 on vaginal shaft 111 is secured by moving stay lock 110 from its open position to its closed position. Excess wire or metal thread is cut at position 112.

In the preferred embodiments shown, the support harness 31, vaginal shaft 35, and stay 38 are made of a material that is biologically compatible such as those well known in the art [stainless steel, titanium or polypropylene plastic] or coated with a biologically compatible material [polyurethane or silicone]. In the embodiments described above wherein the separate components are made on one or more units, it will be appreciated that each such unit will be of a biologically compatible material. Further, whether a unitary or multi-piece design, the PUSH apparatus may be made of a shapeable, superelastic or thermomemory material [titanium-nickel alloy]. In all described embodiments, the preferred design of the support harness includes a means for traction against the pubic bone, allowance for the support harness to be hooked onto the pubic bone, or adapted to clamp onto the pubic bone. In all embodiments illustrated, the stay is of a particular shape to avoid vaginal wall tear, yet be able to be securely fastened and stayed. The serrated surface 40 and the relatively large flat surface of the stay maintain the position of stay 38 and avoid tissue damage, respectively. Damage to the urethra is avoided by the lengthy, uninterrupted rounded surface of the stay, which is positioned adjacent to the urethra.

While the invention has been described in connection with several embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus for treatment of female stress urinary incontinence (SUI) comprising:
   a support harness adapted to fit over the superior edge of the pubic bone of a patient, left or right of the pubis symphysis;
   a stay adapted to rest against the anterior vaginal wall of a patient at the level of the urethrovesical junction;
   a shaft connecting the stay to the support harness and adapted to elevate the stay causing elevation of the anterior vaginal wall; and
   coupling interfaces between the support harness and shaft, and shaft and stay.

2. An apparatus for treatment of SUI as claimed in 1 wherein the shaft and the stay are in fixably adjustable relation.

3. An apparatus for treatment of SUI as claimed in 1 wherein the support harness and the shaft are in fixably adjustable relation.

4. An apparatus for treatment of SUI as claimed in 1 wherein the support harness, shaft and stay are constructed of material that is biologically compatible.

5. An apparatus for treatment of SUI as claimed in 1 wherein the support harness is constructed of material that is shapeable.

6. An apparatus for treatment of SUI as claimed in 1 wherein the support harness has an anterior end and the anterior end has an interior surface, the interior surface of the anterior end of the support harness is adapted to produce traction against the pubic bone.

7. An apparatus for treatment of SUI as claimed in 1 wherein the shaft is constructed of wire or metal thread.

8. An apparatus for treatment of SUI as claimed in 1 wherein the support harness is constructed of superelastic or thermomemory material.

9. An apparatus for treatment of SUI as claimed in 1 wherein the support harness is adapted to hook onto the pubic bone.

10. An apparatus for treatment of SUI as claimed in 1 wherein the support harness is adapted to clamp onto the pubic bone.

11. An apparatus for treatment of female stress urinary incontinence comprising of a single component adapted to form a support harness that fits over the superior edge of the pubic bone of a patient; a stay adapted to engage and elevate the anterior vaginal wall at the level of the urethrovesical junction; and shaft connecting the support harness and stay.

12. An apparatus for treatment of SUI as claimed in 11 wherein the apparatus is constructed of material that is biologically compatible.

13. An apparatus for treatment of SUI as claimed in 11 wherein the apparatus is constructed of material that is shapeable.

14. An apparatus for treatment of SUI as claimed in 11 wherein the support harness has an anterior end and the anterior end has an interior surface, the interior surface of the anterior end of the support harness to be is adapted to produce traction against the pubic bone.

15. An apparatus for treatment of SUI as claimed in 11 wherein the apparatus is constructed of superelastic or thermomemory material.

16. A method for the treatment of SUI comprising the steps of, but not necessarily in the order of:
(a) Placing patient in the lithotomy position;
(b) Assembling a stay and vaginal shaft into an assembled apparatus and loading the assembled apparatus into a cannula delivery unit having a sharp closed leading end;
(c) Penetrating the vaginal wall with the sharp closed leading end of the cannula delivery unit;
(d) Directing the cannula delivery unit in a cephalad direction with the leading end adjacent to the posterior aspect of the pubic bone;
(e) Making a small suprapubic incision lateral to the midline on the same side as the placement of the cannula delivery unit;
(f) Delivering the cannula delivery unit through the incision;
(g) Removing the cannula delivery unit suprapubically, confirming that the stay is correctly and firmly positioned against the anterior vaginal wall;
(h) Raising the stay-vaginal shaft through the suprapubic incision to an appropriate tension;
(i) Attaching the stay-vaginal shaft to a support harness forming a PUSH apparatus, at the suprapubic incision site;
(j) Directing the PUSH apparatus over the pubic bone;
(k) Adjusting the position of the vaginal shaft in the support harness to achieve the appropriate anterior vaginal wall elevation;
(l) Closing the suprapubic incision and, if required, trimming excess shaft length before closing; and
(m) Repeating steps (b)–(l) on the opposite side of the urethrovesical junction using a second PUSH apparatus.

17. A method for the treatment of SUI comprising the steps of, but not necessarily in the order of:
(a) Placing patient in the lithotomy position;
(b) Forming a vaginal wall stay from the vaginal end of an assembly having a vaginal end and a leading end;
(c) Loading the assembly into a cannula delivery unit having a sharp closed leading end;
(d) Penetrating the vaginal wall with the sharp closed leading end of the cannula delivery unit;
(e) Directing the cannula delivery unit in a cephalad direction with the leading end adjacent to the posterior aspect of the pubic bone;
(f) Making a small suprapubic incision lateral to the midline on the same side as the placement of the cannula delivery unit;
(g) Delivering the cannula delivery unit through the incision;
(h) Removing the cannula delivery unit suprapubically;
(i) Positioning the stay firmly against the vaginal wall;
(j) Raising the assembly through the suprapubic incision to an appropriate vaginal wall elevation;
(k) Maintaining the appropriate vaginal wall elevation, directing the leading end of the assembly over the superior edge of the pubic bone;
(l) Closing the suprapubic incision;
(m) Repeating steps (b)–(l) on the opposite side of the urethrovesical junction using a second assembly.

18. A method for the treatment of SUI comprising the steps of, but not necessarily in the order of:
(a) Placing patient in the lithotomy position;
(b) Penetrating the anterior vaginal wall with a directional cannula delivery unit containing an assembly having a support harness end and vaginal shaft;
(c) Directing the cannula delivery unit in a cephalad direction along the posterior aspect of the pubic bone over the superior edge of the pubic bone,
(d) Advancing the support harness end of the assembly through the cannula delivery unit down the anterior aspect of the pubic bone until the cannula delivery unit rests at a position approximately halfway down the anterior aspect of the pubic bone;
(e) Withdrawing the cannula delivery unit from the vagina exposing a portion of the vaginal shaft;
(f) Coupling a stay on the vaginal shaft;
(g) Adjusting the position of the stay against the anterior vaginal wall until the appropriate vaginal wall elevation is achieved;
(h) Securing the position of the stay and trimming excess vaginal shaft from the assembly; and
(i) Repeat steps (b)–(h) on the opposite side of the urethrovesical junction using a second assembly.

* * * * *